United States Patent [19]
Inaba et al.

[11] 3,980,645
[45] Sept. 14, 1976

[54] FUSED QUINAZOLINONES AND A PROCESS FOR PRODUCTION THEREOF

[75] Inventors: Shigeho Inaba, Takarazuka; Michihiro Yamamoto, Toyonaka; Kikuo Ishizumi, Ikeda; Kazuo Mori, Kobe; Masao Koshiba, Takarazuka; Hisao Yamamoto, Nishinomiya, all of Japan

[73] Assignee: Sumitomo Chemical Company, Limited, Osaka, Japan

[22] Filed: Nov. 7, 1974

[21] Appl. No.: 521,768

Related U.S. Application Data

[60] Division of Ser. No. 381,571, July 23, 1973, Pat. No. 3,891,638, which is a continuation-in-part of Ser. No. 172,562, Aug. 17, 1971, abandoned.

[30] Foreign Application Priority Data

Aug. 27, 1970  Japan.............................. 45-75817
Sept. 16, 1970  Japan.............................. 45-81593

[52] U.S. Cl........................ 260/244 R; 260/251 A
[51] Int. Cl.².............. C07D 265/00; C07D 273/00; C07D 295/00
[58] Field of Search............................ 260/244

[56] References Cited
UNITED STATES PATENTS 3,329,679  7/1967  Sulkowski et al................ 260/256.4

FOREIGN PATENTS OR APPLICATIONS 249,066  9/1966  Austria
249,068  9/1966  Austria OTHER PUBLICATIONS
Sato et al.–"Yakugaku Zasshi" 90(5) pp. 629–633 (1970)–Synthesis of Quinazolinone Derivatives.

*Primary Examiner*—James O. Thomas, Jr.
*Assistant Examiner*—D. W. Robinson
*Attorney, Agent, or Firm*—Stevens, Davis, Miller & Mosher

[57] ABSTRACT
Fused quinazolinone derivatives of the formula,

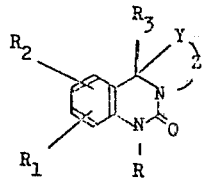

wherein $R_1$ and $R_2$ are individually hydrogen, $C_{1-4}$ alkyl, $C_{1-4}$ alkoxy, nitro, $C_{1-4}$ alkylsulfonyl or halogen; $R_3$ is pyridyl, thienyl or a group of the formula

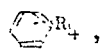

wherein $R_4$ is hydrogen or halogen; R is hydrogen, $C_{1-4}$ alkyl, $C_{2-5}$ alkenyl, aralkyl, $(C_{3-6}$ cycloalkyl)$C_{1-4}$ alkyl, $(C_{1-4}$ alkoxy)$C_{1-4}$ alkyl, $(C_{1-4}$ alkylthio)$C_{1-4}$ alkyl, hydroxy-$C_{1-4}$ alkyl or $C_{2-5}$ alkanoyloxy-$C_{1-4}$ alkyl; Y is oxygen, or a group of the formula $N - R_5$, wherein $R_5$ is hydrogen or $C_{1-4}$ alkyl; and Z is $C_{2-5}$ alkylene or alkenylene, are prepared by reacting a trihaloacetamidophenyl ketone derivative of the formula,

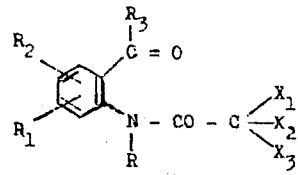

wherein $R_1$, $R_2$, $R_3$ and R are as defined above; and $X_1$, $X_2$ and $X_3$ are halogen, with an amine of the formula, $HY - Z - NH_2$, wherein Y and Z are as defined above, or a salt thereof, in the presence of a solvent or a mixture thereof. They have remarkable pharmacological properties such as anti-inflammatory, analgesic and/or uricosuric activities.

2 Claims, No Drawings

FUSED QUINAZOLINONES AND A PROCESS FOR PRODUCTION THEREOF

CROSS REFERENCE TO THE RELATED APPLICATION

This application is a division of application Ser. No. 381,571 filed July 23, 1973, now U.S. Pat. No. 3,891,638, which is a continuation in part of application Ser. No. 172,562 filed Aug. 17, 1971, now abandoned.

This invention relates to quinazolinone derivatives and a process for production thereof.

More particularly, the present invention relates to fused quinazolinone derivatives of the formula,

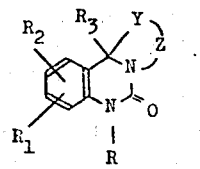

(I)

wherein $R_1$ and $R_2$ are individually a hydrogen atom, a $C_{1-4}$ alkyl group, a $C_{1-4}$ alkoxy group, a nitro group, a $C_{1-4}$ alkylsulfonyl group or a halogen atom; $R_3$ is a group of the formula

(wherein $R_4$ is a hydrogen atom or a halogen atom), a pyridyl group or a thienyl group; R is a hydrogen atom, a $C_{1-4}$ alkyl group, a $C_{2-5}$ alkenyl group, an aralkyl group, a $C_{3-6}$ cycloalkyl-$C_{1-4}$ alkyl group, a $C_{1-4}$ alkoxy $C_{1-4}$ alkyl group, a $C_{1-4}$ alkylthio-$C_{1-4}$ alkyl group, a hydroxy-$C_{1-4}$ alkyl group or a $C_{2-5}$ alkanoyloxy-$C_{1-4}$ alkyl group; Y is an oxygen atom or a group of the formula N - $R_5$ (wherein $R_5$ is a hydrogen atom or a $C_{1-4}$ alkyl group); and Z is a $C_{2-5}$ alkylene or alkenylene group, which may contain among the carbon chain one oxygen atom, and may be optionally substituted by one or two $C_{1-4}$ alkyl groups, and further, the two alkyl groups on adjacent carbon atoms of the alkylene or alkenylene group may be joined to form a benzene ring, and a process for production and pharmaceutical use of the same.

In the compounds of the formula (I), the term "alkyl" means both straight and branched chain aliphatic hydrocarbon radicals, and the $C_{1-4}$ alkyl group includes, for example, methyl, ethyl, n-propyl, isopropyl, n-butyl isobutyl and tertiary-butyl groups; the aralkyl group includes, for example, benzyl, phenetyl, methoxy benzyl, chlorobenzyl and fluorobenzyl groups; the $C_{1-4}$ alkoxy group includes, for example, methoxy, ethoxy, n-propoxy, isopropoxy, n-butoxy and tertiary-butoxy groups; the $C_{1-4}$ alkylthio group includes, for example, methylthio, ethylthio and isopropylthio groups, the $C_{2-5}$ alkanoyloxy group includes, for example, acetoxy, propionyloxy and isobutyryloxy groups; the $C_{2-5}$ alkenyl group includes, for example, vinyl, allyl, methallyl, butenyl and crotyl groups; and the $C_{3-6}$ cycloalkyl group includes, for example, cyclopropyl, cyclobutyl, cyclopentyl and cyclohexyl groups.

The quinazolinone derivatives of the formula (I), which include novel compounds, have remarkable pharmacological properties, such as anti-inflammatory, analgesic and/or uricosuric activities.

Particularly, the present inventors have found that novel quinazolinone derivatives of the formula,

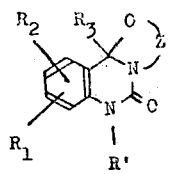

(I - a)

wherein $R_1$, $R_2$, $R_3$ and Z are as defined above; and R' has the same definition as that of R defined above except that R' can not be a hydrogen atom, possess much more excellent anti-inflammatory and/or uricosuric effects in animal tests with low toxicity. Illustratively, 9-chloro-2,3,6,10b-tetrahydro-6-methyl-10b-phenyl-5H-oxazolo[3,2-C]-quinazolin-5-one shows remarkable inhibitory action for carrageenin-induced edema in rat, while no toxic symptoms are observed and occult bleeding is negative in feces after oral administration of 2,000 mg/kg in rat. The anti-inflammatory activity of the present compound is more effective than that of 1,2-diphenyl-3,5-dioxo-4-(n-butyl)-pyrozolidine (phenylbutazone), and the acute, subacute and chronic toxicities of the present compound are much lower than those of phenylbutazone. Moreover, this compound possesses more marked uricosuric activity than the known drugs such as p-(dipropylsulfamoyl)benzoic acid (probenecid).

Thus, an object of the present invention is to provide a novel and useful process for producing commercially such valuable compounds. Another object of the present invention is to provide novel quinazolinone derivatives of the formula (I-a) excellent in anti-inflammatory and/or uricosuric effects. Other object of the present invention is to provide a pharmaceutically acceptable composition containing one or more quinazolinone derivatives of the formula (I-a), and a pharmaceutically acceptable diluent or carrier. Further objects of the present invention will be apparent from the accompanying disclosure and discussion.

In order to accomplish these objects, the present invention provides a process for producing quinazolinone derivatives of the formula (I), which comprises contacting a trihaloacetamidophenyl ketone derivative of the formula,

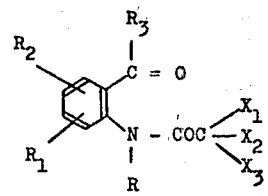

(II)

wherein $R_1$, $R_2$, $R_3$ and R are the same as defined above; and $X_1$, $X_2$ and $X_3$ are same or different halogen atoms, with an amine of the formula,

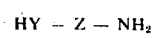

(III)

wherein Y and Z are the same as defined above, or a salt thereof.

A trihaloacetamidophenyl ketone derivative of the formula (II) can, for example, be prepared by contacting a corresponding 2-aminophenyl ketone derivative of the formula,

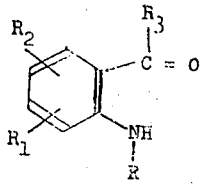

(IV)

wherein $R_1$, $R_2$, $R_3$ and R are the same as defined above, with a trihaloacetic acid or a reactive derivative thereof.

In preparing a quinazolinone derivative of the formula (I) according to the process of the present invention, a trihaloacetamidophenyl ketone derivative of the formula (II) is reacted with an amine of the formula (III) or a salt thereof, preferably in the presence of a solvent or solvent mixture.

Suitable solvents are, for example, methanol, ethanol, isopropanol, tertiary-butanol, Cellosolve, pyridine, dimethyl sulfoxide and dimethylformamide. Excess of the amine of the formula (III) may be also used as a solvent.

When a salt of the amine of the formula (III) is employed, it is desirable to carry out the reaction in the presence of a base, which may include an inorganic base such as sodium hydroxide, potassium hydroxide, sodium carbonate or potassium carbonate, or an organic base such as pyridine, triethylamine, tri-n-propylamine or dimethylaniline.

Generally, the reaction may proceed at room temperature, but higher or lower temperatures may be employed satisfactorily.

A quinazolinone derivative of the formula,

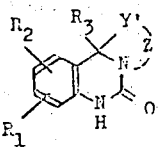

(I-b)

wherein $R_1$, $R_2$, $R_3$ and Z are the same as defined above; and Y' has the same definition as that of Y defined above except that Y' can not be a group of the formula NH, which is obtained according to the above-mentioned process may be further converted to a corresponding N-substituted quinazoline derivative of the formula,

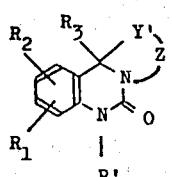

(I-c)

wherein $R_1$, $R_2$, $R_3$, Y' and Z are the same as defined above; and R' has the same definition as that of R defined above except that R' cannot be a hydrogen atom, by reaction with a reactive derivative of the compound of the formula, $$R' - OH \qquad (V)$$

wherein R' is the same as defined above.

As the reactive derivative, there may be preferably employed a halide such as chloride, bromide or iodide; a sulfonate such as p-toluenesulfonate or trichloromethanesulfonate; or a sulfate such as dimethyl sulfate or diethyl sulfate.

The reaction can be carried out by treating a quinazolinone derivative of the formula (I-b) with a reactive derivative of the compound of the formula (V) in the presence of a base, or alternatively by treating the quinazoline derivative with a base to obtain a basic metal salt thereof and then treating the resulting metal salt with the reactive derivative of the formula (V).

Preferable bases in above reaction include, for example, alkali metal hydrides such as sodium hydride or potassium hydride; alkali metal amides such as sodium amide or potassium amide; organolithium compounds such as butyl lithium or phenyl lithium; and alkali metal alkoxides such as sodium methoxide, potassium methoxide, sodium ethoxide, potassium ethoxide or potassium tertiary-butoxide.

The reaction is preferably effected in an organic solvent or solvent mixture. The suitable solvents include, for example, benzene, toluene, xylene, dimethylformamide, dimethylacetamide, ether, tetrahydrofuran, diglyme, acetone and dimethylsulfoxide, and a mixture thereof.

The reaction is generally effected at a temperature within a range of from about room temperature to the boiling point of the solvent employed.

According to the process of the present invention, there are obtained, for example, the following quinazolinone derivatives:

1,2,3,10b-Tetrahydro-10b-phenyl-imidazo[1,2-C]quinazolin-5(6H)-one

9-Fluoro-1,2,3,10b-tetrahydro-10b-phenyl-imidazo [1,2-C]quinazolin-5(6H)-one

9-Chloro-1,2,3,10b-tetrahydro-10b-phenyl-imidazo [1,2-C]quinazolin-5(6H)-one

9-Bromo-1,2,3,10b-tetrahydro-10b-phenyl-imidazo [1,2-C]quinazolin-5(6H)-one

8-Chloro-1,2,3,10b-tetrahydro-10b-phenyl-imidazo [1,2-C]quinazolin-5(6H)-one

7-Chloro-1,2,3,106-tetrahydro-10b-phenyl-imidazo [1,2-C]quinazolin-5(6H)-one 7,9-Dichloro-1,2,3,10b-tetrahydro-10b-phenyl-imidazo [1,2-C]quinazolin-5(6H)-one 9-Chloro-1,2,3,10b-tetrahydro-10b-(o-fluorophenyl)-imidazo [1,2-C]quinazolin-5(6H)-one 9-Methyl-1,2,3,10b-tetrahydro-10b-phenyl-imidozo [1,2-C]quinazolin-5(6H)-one 9-Nitro-1,2,3,10b-tetrahydro-10b-phenyl-imidazo [1,2-C]quinazolin-5(6H)-one 9-Chloro-1,2,3,10b-tetrahydro-1-methyl-10b-phenyl-imidazo[1,2-C]quinazolin-5(6H)-one 9-Chloro-1,2,3,10b-tetrahydro-6-methyl-10b-phenyl-imidazo[1,2-C]quinazolin-5(6H)-one 9-Nitro-1,2,3,10b-tetrahydro-6-methyl-10b-phenyl-imidazo[1,2-C]quinazolin-5(6H)-one 9-Methoxy-1,2,3,10b-tetrahydro-6-cyclopropylmethyl-10b-phenyl-imidazo[1,2-C]quinazolin-5(6H)-one 9-Chloro-1,2,3,10b-tetrahydro-1,6-dimethyl-10b-phenyl-imidazo[1,2-C]quinazolin-5(6H)-one 9-Chloro-1,2,3,10b-tetrahydro-10b-(2-pyridyl)imidazo[1,2-C]quinazolin-5(6H)-one 9-Chloro-1,2,3,10b-tetrahydro-10b-(2-thienyl)-imidazo[1,2-C]quinazolin-5(6H)-one 1,2,3,4,7,11b-Hexahydro-11b-phenyl-6H-pyrimido[1,2-C]quinazolin-6-one 10-Methoxy-1,2,3,4,7,11b-hexahydro-11b-phenyl 6H-pyrimido[1,2-C]quinazolin-6-one 10-Chloro-1,2,3,4,7,11b-hexahydro-11b-phenyl-6H-pyrimido[1,2-C]quinazolin-6-one 10-Chloro-1,2,3,4,7,11b-hexahydro-1,7-dimethyl-11b-phenyl-6H-pyrimido[1,2-C]quinazolin-6-one 10-Chloro-1,2,3,4,7,11b-hexahydro-1-methyl-7-cyclopropylmethyl-11b-phenyl-6H-pyrimido[1,2-C]quinazolin-6-one 10-Chloro-1,2,3,4,7,11b-hexahydro-11b-(2-thienyl)-6H-pyrimido[1,2-C]quinazolin-6-one 10-Chloro-1,2,3,4,7,11b-hexahydro-7-methyl-11b-phenyl-6H-pyrimido[1,2-C]quinazolin-6-one 11-Chloro-1,2,3,4,5,12b-hexahydro-12b-phenyl-[1,3]diazepino[1,2-C]quinazolin-7(8H)-one 11-Chloro-1,2,3,4,5,12b-hexahydro-1,8-dimethyl-12b-phenyl-[1,3]diazepino[1,2-C]quinazolin-7(8H)-one 12-Chloro-1,3,4,5,6,13b-hexahydro-13b-phenyl-2H-[1,3]diazocino[1,2-C]quinazolin-8(9H)-one 2,3,6,10b-Tetrahydro-10b-phenyl-5H-oxazolo[3,2-C]quinazolin-5-one 9-Methoxy-2,3,6,10b-tetrahydro-10b-phenyl-5H-oxazolo[3,2-C]quinazolin-5-one 9-Chloro-2,3,6,10b-tetrahydro-10b-phenyl-5H-oxazolo[3,2-C]quinazolin-5-one 7,9-Dichloro-2,3,6,10b-tetrahydro-10b-phenyl-5H-oxazolo[3,2-C]quinazolin-5-one 9-Methyl-2,3,6,10b-tetrahydro-10b-phenyl-5H-oxazolo[3,2-C]quinazolin-5-one 9-Nitro-2,3,6,10b-tetrahydro-10b-phenyl-5H-oxazolo[3,2-C]quinazolin-5-one 9-Methylsulfonyl-2,3,6,10b-tetrahydro-10b-phenyl-5H-oxazolo[3,2-C]quinazolin-5-one 9-Chloro-2,3,6,10b-tetahydro-10b-(2-pyridyl)-5H-oxazolo[3,2-C]quinazolin-5-one 9-Bromo-2,3,6,10b-tetrahydro-10b-(2pyridyl) 5H-oxazolo[3,2-C]quinazolin-5-one 9-Chloro-2,3,6,10b-tetrahydro-10b-(2-thienyl) 5H-oxazolo[3,2-C]quinazolin-5-one 9-Chloro-2,3,6,10b-tetrahydro-6-methyl-10b-phenyl-5H-oxazolo[3,2-C]quinazolin-5-one 9-Chloro-2,3,6,10b-tetrahydro-6-cyclopropylmethyl-10b-phenyl-5-H-oxazolo[3,2-C]quinazolin-5-one 9-Chloro-2,3,6,10b-tetrahydro-2-methyl-10b-phenyl-5H-oxazolo[3,2-C]quinazolin-5-one 9-Nitro-2,3,6,10b-tetrahydro-6-methyl-10b-phenyl-5H-oxazolo[3,2-C]quinazolin-5-one 9-Nitro-2,3,6,10b-tetrahydro-6-benzyl-10b-phenyl-5H-oxazolo[3,2-C]quinazolin-5-one 9-Chloro-2,3,6,10b-tetrahydro-6-methyl-10b-(2-pyridyl)-5H-oxazolo[3,2-C]quinazolin-5-one 9-Chloro-2,3,6,10b-tetrahydro-6-methyl-10b-(2-thienyl)-5H-oxazolo[3,2-C]quinazolin-5-one 9-Chloro-2,3,6,10b-tetrahydro-6-(2-hydroxyethyl)-10b-phenyl-5H-oxazolo[3,2-C]quinazolin-5-one 9-Chloro-2,3,6,10b-tetrahydro-6-(2-ethoxyethyl)-10b-phenyl-5H-oxazolo[3,2-C]quinazolin-5-one 9-Nitro-2,3,6,10b-tetrahydro-6-(2-isopropoxyethyl)-10-phenyl-5H-oxazolo[3,2-C]quinazolin-5-one 9-Chloro-2,3,6,10b-tetrahydro-6-(2-methylthioethyl)-10b-phenyl-5H-oxazolo[3,2-C]quinazolin-5-one 9-Chloro-2,3,6,10b-tetrahydro-6-(2-acetoxyethyl)-10b-phenyl-5H-oxazolo[3,2-C]quinazolin-5-one 3,4,7,11b-Tetrahydro-11b-phenyl-2H,6H-[1,3]oxazino[3,2-C]quinazolin-6-one 10-Chloro-3,4,7,11b-tetrahydro-11b-phenyl-2H,6H-[1,3]oxazino[3,2-C]quinazolin-6-one 10-Chloro-3,4,7,11b-tetrahydro-7-methyl-11b-phenyl-2H,6H-[1,3]oxazino[3,2-C]quinazolin-6-one 10-Chloro-3,4,7,11b-tetrahydro-7-allyl-11b-phenyl-2H,6H-[1,3]oxazino[3,2-C]quinazolin-6-one 10-Nitro-3,4,7,11b-tetrahydro-7-methyl-11b-phenyl-2H,6H-[1,3]oxazino[3,2-C]quinazolin-6-one 10-Chloro-3,4,7,11b-tetrahydro-7-methoxymethyl-11b-phenyl-2H,6H-[1,3]oxazino[3,2-C]quinazolin-6-one 10-Nitro-3,4,7,11b-tetrahydro-7-methyl-10b-phenyl-2H,6H-[1,3]oxazino[3,2-C]quinazolin-6-one 10-Chloro-3,4,7,11b-tetrahydro-7-methyl-11b-(o-fluorophenyl)-2H,6H-[1,3]oxazino[3,2-C]quinazolin-6-one 10-Nitro-3,4,7,11b-tetrahydro-7-(2-acetoxyethyl)-11b-phenyl-2H,6H-[1,3]oxazino[3,2-C]quinazolin-6-one 10-Nitro-3,4,7,11b-tetrahydro-7-(2-hydroxyethyl)-11b-phenyl-2H,6H-[1,3]oxazino[3,2-C]quinazolin-6-one 10-Chloro-3,4,7,11b-tetrahydro-7-methyl-11b-(2-pridyl)-2H,6H-[1,3]oxazino[3,2-C]quinazolin-6-one 11-Chloro-2,3,4,5,8,12b-hexahydro-12b-phenyl-7H-[1,3]oxazepino[3,2-C]quinazolin-7-one 11-Chloro-2,5,8,12b-tetrahydro-12b-phenyl-7H-[1,3]oxazepino[3,2-C]quinazolin-7-one 11-Chloro-2,3,4,5,8,12b-hexahydro-8-methyl-12b-phenyl-7H-[1,3]oxazepino[3,2-C]quinazolin-7-one 12-Chloro-2,3,5,6,9,13b-hexahydro-13b-phenyl-8H-[1,6,3]dioxazocino[3,2-C]quinazolin-8-one 12-Chloro-2,3,5,6,9,13b-hexahydro-9-methyl-13b-phenyl- 8H-[1,6,3,]dioxazocino[3,2-C]quinazolin-8-one 11-Chloro-1,12b-dihydro-12b-phenyl-benzimidazo[1,2-C]quinazolin-7(8H)-one 11-Nitro-1,12b-dihydro-12b-phenyl-benzimidazo [1,2-C]quinazolin-7(8H)-one 11-Chloro-1,12b-dihydro-1,8-dimethyl-12b-phenyl-benzimidazo[1,2-C]quinazolin-7(8H)-one 11-Chloro-8,12b-dihydro-12b-phenyl-7H-benzoxazolo[3,2-C]quinazolin-7-one 11-Chloro-8,12b-dihydro-8-methyl-12b-phenyl-7H-benzoxazolo[3,2-C]quinazolin-7-one 11-Nitro-8,12b-dihydro-8-methyl-12b-phenyl-7H-benzoxazolo[3,2-C]quinazolin-7-one The present invention is further explained referring to the following examples of more preferred embodiments thereof, which are presented for the purpose of illustration and are not intended to limit the scope of the invention.

EXAMPLE 1

To a solution of 3.77g of 2-trichloroacetamido-5-chlorobenzophenone in 70 ml of ethanol was added 5 ml of ethylenediamine, and the resultant mixture was heated under reflux for 2 hours. After cooling with ice, the resulting crystals were separated by filtration, washed with water and dried to give 2.12 g of 9-chloro-1,2,3,10b-tetrahydro-10b-phenyl-imadazo[1,2-C]quinazolin-5(6H)-one. Recrystallization from ethanol-dimethyl formamide gave colorless needles, having a melting point of 274° – 275°C.

EXAMPLE 2

To a solution of 1.89 g of 2-trichloroacetamido-5-chlorobenzophenone in 50 ml of ethanol was added 2.22 g of 1,3-diaminopropane, and the resultant mixture was allowed to stand at room temperature overnight. Then, the reaction mixture was poured into 300 ml of water, and the precipitate thus formed was separated by filtration, washed with ether and dried to give 1.25 g of 10-chloro-1,2,3,4,7,11b-hexahydro-11b-phenyl-6H-pyrimido[1,2-C]quinazolin-6-one, having a melting point of 275° – 276°C.

EXAMPLE 3

Using a procedure similar to that described in Example 1, but replacing ethylenediamine by N-methylethylenediamine, there was obtained 9-chloro-1,2,3,10b-tetrahydro-1-methyl-10b-phenylimidazo[1,2-C]quinazolin-5(6H)-one, having a melting point of 270° – 271°C.

EXAMPLE 4

To a solution of 1.89 g of 2-trichloroacetamido-5-chlorobenzophenone in 40 ml of dimethylsulfoxide was added 3.05 g of monoethanolamine, and the resultant mixture was heated at about 90°C for 3 hours. After cooling, the reaction mixture was poured into 300 ml of water and extracted with chloroform. The extract was washed twice with water and dried over anhydrous sodium sulfate. The solvent was removed under reduced pressure. The residue was chromatographed on silica gel using chloroform as an eluent to give 1.0 g of 9-chloro-2,3,6,10b-tetrahydro-10b-phenyl-5H-oxazolo[3,2-C]quinazolin-5-one. Recrystallization from ethanol gave pale yellow prisms, having a melting point of 219° – 220°C.

EXAMPLE 5

To a solution of 3.77 g of 2-trichloroacetamido-5-chlorobenzophenone in 100 ml of ethanol was added 3.05 g of monoethanolamine, and the resulting mixture was refluxed for 2 hours. Then, the solvent was removed under reduced pressure. The residue was chromatographed on silica gel using chloroform as an eluent to give 2.25 g of 9-chloro-2,3,6,10b-tetrahydro-10b-phenyl-5H-oxazolo[3,2-C]quinazolin-5-one, having a melting point of 216° – 217°C.

EXAMPLE 6

Using a procedure similar to that described in Example 5, but replacing 2-trichloroacetamido-5-chlorobenzophenone by 2-(N-methyl-trichloroacetamido)-5-chlorobenzophenone, there was obtained 9-chloro-2,3,6,10b-tetrahydro-6-methyl-10b-phenyl-5H-oxazolo[3,2-C]quinazolin-5-one, having a melting point of 124° – 125°C.

EXAMPLE 7

To a solution of 1.27 g of 2-trichloroacetamido-5-bromophenyl 2-pyridyl ketone in 20 ml of dimethylsulfoxide was added 1.83 g of monoethanolamine, and the resultant mixture was heated in an oil bath at 100°C (bath temperature) for 3 hours. After cooling, the reaction mixture was poured into 100 ml of water and the resulting mixture was extracted with dichloromethane. The extract was washed with water and dried over anhydrous sodium sulfate. The solvent was removed under reduced pressure. The residue was chromatographed on silica gel using chloroform as an eluent to give 0.6 g of 9-bromo-2,3,6,10b-tetrahydro-10b-(2-pyridyl)-5H-oxazolo[3,2-C]quinazolin-5-one, having a melting point of 241° – 242°C.

EXAMPLE 8

To a solution of 3.77 g of 2-trichloroacetamido-5-chlorobenzophenone in 50 ml of dimethylsulfoxide was added 5.26 g of 2-(2-hydroxyethoxy)ethylamine, and the mixture was heated at 105°C for 3 hours. After cooling, the reaction mixture was poured into 300 ml of water and the resulting mixture was extracted with chloroform. The extract was washed with water and dried over anhydrous sodium sulfate. The solvent was removed under reduced pressure. The residue was chromatographed on silica gel using ethyl acetate as an eluent to give 2.4 g of a colorless oil, which was crystalized from petroleum benzin-ethanol to yield 12-chloro-2,3,5,6,9,13b-hexahydro-13b-phenyl-8H-[1,6,3,]dioxazocino[3,2-C]quinazolin-8-one, having a melting point of 212° – 214°C.

EXAMPLE 9

To a solution of 1.89 g of 2-trichloroacetamido-5-chlorobenzophenone in 40 ml of dimethylsulfoxide was added 3.25 g of o-phenylenediamine, and the resultant mixture was heated at 100°C for 13 hours. After cooling, the reaction mixture was poured into 200 ml of water and the precipitates were separated by filtration, washed successively with water and ether, and dried to give 0.86 g of light brown crystals, which were recrystallized from acetone-dimethylformamide to yield colorless fine needles of 11-chloro-1,12b-dihydro-12b-phenyl-benzimidazo[1,2-C]quinazolin-7(8H)-one, having a melting point of above 300°C.

EXAMPLE 10

To a solution of 1.5 g of 9-chloro-2,3,6,10b-tetrahydro-10b-phenyl-5H-oxazolo[3,2-C]quinazolin-5-one in 20 ml of dimethylformamide was added 0.21 g of 62.5% sodium hydride. The resultant mixture was stirred with heating at 50° – 55°C for 1 hour, and 1.42 g of methyl iodide was added thereto at room temperature. Then, the mixture was heated at 55° – 60°C for 3 hours. After cooling, the reaction mixture was poured into 100 ml of water and acidified with hydrochloric acid. The resulting mixture was extracted with 50 ml of chloroform and the chloroform layer was washed successively with dilute hydrochloric acid and water, and dried over anhydrous sodium sulfate. The solvent was removed under reduced pressure. The residue was chromatographed on silica gel using chloroform as an eluent to give 1.2 g of 9-chloro-2,3,6,10b-tetrahydro-6-methyl-10b-phenyl-5H-oxazolo[3,2-C]quinazolin-5-one, having a melting point of 124° – 125°C. Recrystallization from ethanol gave colorless prisms, having a melting point of 136° – 137°C.

EXAMPLE 11

To a solution of 3.61 g of 9-chloro-2,3,6,10b-tetrahydro-10b-phenyl-5H-oxazolo[3,2-C]quinazolin-5-one in 80 ml of dimethylformamide was added 0.50 g of 64% sodium hydride. The resultant mixture was stirred with heating at 100°C for 30 minutes and 2.3 g of 90% cyclopropylmethyl bromide was added thereto at room temperature. Then, the mixture was heated at 100°C for 5 hours. After cooling, the reaction mixture was poured into 400 ml of water. The resulting mixture was extracted with chloroform and the chloroform layer was washed twice with dilute hydrochloric acid, and dried over anhydrous sodium sulfate. The solvent was removed under reduced pressure. The residue was crystallized from ethanol to give 3.05 g of colorless prisms of 9-chloro-2,3,6,10b-tetrahydro-6-cyclopropylmethyl-10b-phenyl-5H-oxazolo[3,2-C]quinazolin-5-one, having a melting point of 143° – 144°C.

EXAMPLE 12

To a solution of 7.75 g of 2-trichloroacetamido-5-nitrobenzophenone in 50 ml. of dimethylsulfoxide was added 1.47 g of monoethanolamine, and the mixture was heated at 100°C for 2 hours. After cooling, the reaction mixture was poured into 500 ml. of water and the resulting precipitate was collected by filtration, washed successively with water and ether to give 3.52 g of 9-nitro-2,3,6,10b-tetrahydro-10b-phenyl-5H-oxazolo[3,2-C]quinazolin-5-one, having a melting point of 275°–276°C.

EXAMPLE 13

Using a procedure similar to that described in Example 12, but replacing 2-trichloroacetamido-5-nitrobenzophenone by 2-trichloroacetamido-5-chlorophenyl 2-thienyl ketone, there was obtained 9-chloro-2,3,6,10b-tetrahydro-10b-(2-thienyl)-5H-oxazolo[3,2-C]quinazolin-5-one, having a melting point of 193°–194°C.

EXAMPLE 14

To a solution of 0.93 g of 9-nitro-2,3,6,10b-tetrahydro-10b-phenyl-5H-oxazolo[3,2-C]quinazolin-5-one in 10 ml. of dimethylfomamide was added 0.18 g of 52.9% sodium hydride. The mixture was stirred with heating at 60°C for 1 hr. then, 0.68 g of benzyl bromide was added thereto. The resulting mixture was heated at 100°C for 4 hours. After cooling, the reaction mixture was poured into 50 ml. of water and the resulting precipitates were collected by filtration, washed with water and dried. The crude product was recrystallized from a mixture of methanol and carbon tetrachloride to give 1.0 g of 9-nitro-2,3,6,10b-tetrahydro-6-benzyl-10b-phenyl-5H-oxazolo[3,2-C]quinazolin-5-one as yellowish brown prisms, having a melting point of 96°–98°C (decomp.).

EXAMPLE 15

Using a procedure similar to that described in Example 14, but replacing benzyl bromide by methyl iodide, there was obtained 9-nitro-2,3,6,10b-tetrahydro-6-methyl-10b-phenyl-5H-oxazolo[3,2-C]quinazolin-5-one as pale yellow scales, having a melting point of 135.5°–136.5°C.

EXAMPLE 16

Using a procedure similar to that described in Example 14, but replacing benzyl bromide by 2-isopropoxyethyl chloride, there was obtained 9-nitro-2,3,6,10b-tetrahydro-6-(2-isopropoxyethyl)-10b-phenyl-5H-oxazolo [3,2-C]quinazolin-5-one as yellow scales having a melting point of 123°–124°C.

EXAMPLE 17

Using a procedure similar to that described in Example 11, but replacing cyclopropylmethyl bromide by 2-methylthioethyl chloride, there was obtained 9-chloro-2,3,6,10b-tetrahydro-6-(2-methylthioethyl)-10b-phenyl-5H-oxazolo[3,2-C]quinazolin-5-one as colorless needles, having a melting point of 145°–146°C.

EXAMPLE 18

Using a procedure similar to that described in Example 11, but replacing cyclopropylmethyl bromide by 2-acetoxyethyl chloride, there was obtained 9-chloro-2,3,6,10b-tetrahydro-6-(2-acetoxyethyl)-10b-phenyl-5H-oxazolo [3,2-C]quinazolin-5-one as colorless prisms, having a melting point of 121°–123°C.

EXAMPLE 19

To a suspension of 11.3 g of 2-trichloroacetamido-5-chlorobenzophenone in 100 ml. of ethanol was added 4.51 g of 3-amino-1-propanol. The mixture was heated under reflux for 3 hours. Then, 1.7 g of potassium hydroxide was added thereto and the resulting mixture was further refluxed for 3 hours. After cooling, the precipitate was filtered off and washed with ethanol. The filtrate was concentrated under reduced pressure and to the residue was added 200 ml. of water. The resulting solid was collected by filtration, washed with water and dried to give 9.87 g of 10-chloro-3,4,7,11b-tetrahydro-11b-phenyl-2H,6H-[1,3]oxazino[3,2-C]quinazolin-6-one. Recrystallization from ethanol gave pale yellow prisms, having a melting point of 202°–203.5°C.

EXAMPLE 20

Using a procedure similar to that described in Example 19, there was obtained 2,3,6,10b-tetrahydro-10b-phenyl-5H-oxazolo[3,2-C]quinazolin-5-one as colorless fine crystals, having a melting point of 193.5°–194.5°C.

EXAMPLE 21

Using a procedure similar to that described in Example 12, there were obtained the following compounds;
9-methyl-2,3,6,10b-tetrahydro-10b-phenyl-5H-oxazolo[3,2-C]quinazolin-5-one, m.p. 247°–248°C;
10-methoxy-3,4,7,11b-tetrahydro-11b-phenyl-2H,6H-[1,3]oxazino[3,2-C]quinazolin-6-one, m.p. 215.5°–216.5°C;
10-chloro-3,4,7,11b-tetrahydro-11b-(o-fluorophenyl)-2H,6H-[1,3]oxazino[3,2-C]quinazolin-6-one, m.p. 231° – 232°C; and
10-methylsulfonyl-3,4,7,11b-tetrahydro-11b-phenyl-2H,6H-[1,3]oxazino[3,2-C]quinazolin-6-one, m.p. 297°–298°C.

EXAMPLE 22

Using a procedure similar to that described in Example 14, there were obtained the following compounds;
2,3,6,10b-tetrahydro-6-methyl-10b-phenyl-5H-oxazolo[3,2-C]quinazolin-5-one, m.p. 190°–191°C;
6,9-dimethyl-2,3,6,10b-tetrahydro-10b-phenyl-5H-oxazolo[3,2-C]quinazolin-5-one, m.p. 122°–123°C;
9-chloro-2,3,6,10b-tetrahydro-6-(2-hydroxyethyl)-10b-phenyl-5H-oxazolo[3,2-C]quinazolin-5-one, m.p. 116°–117°C;
10-chloro-3,4,7,11b-tetrahydro-7-methyl-11b-phenyl-2H,6H-[1,3]oxazino[3,2-C]quinazolin-6-one, m.p. 178°–179°C;

10-chloro-3,4,7,11b-tetrahydro-7-allyl-11b-phenyl-2H,6H-[1,3]oxazino[3,2-C]quinazolin-6-one, m.p. 112°-113°C;

10-chloro-3,4,7,11b-tetrahydro-7-methoxymethyl-11b-phenyl-2H,6H-[1,3]oxazino[3,2-C]quinazolin-6-one, m.p. 143°144°C;

10-methylsulfonyl-3,4,7,11b-tetrahydro-7-methyl-11b-phenyl-2H,6H-[1,3]oxazino[3,2-C]quinazolin-6-one, m.p. 225°-226°C;

10-methoxy-3,4,7,11b-tetrahydro-7-methyl-11b-phenyl-2H,6H-[1,3]oxazino[3,2-C]quinazolin-6-one, m.p. 152°-153°C; and 10-chloro-3,4,7,11b-tetrahydro-7-methyl-11b-(o-fluorophenyl)-2H,6H-[1,3]oxazino[3,2-C]quinazolin-6-one, m.p. 180.5°-181.5°C.

What is claimed is:

1. A process for producing a quinazolinone derivative of the formula

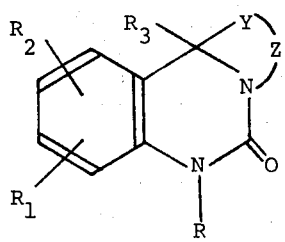

(I)

wherein $R_1$ and $R_2$ are individually a hydrogen atom, a $C_{1-4}$ alkyl group, a $C_{1-4}$ alkoxy group, a nitro group, a $C_{1-4}$ alkylsulfonyl group or a halogen atom; $R_3$ is a pyridyl group, a thienyl group or a group of the formula

wherein $R_4$ is a hydrogen or a halogen atom; R is a hydrogen atom or a $C_{1-4}$ alkyl group; Y is an oxygen atom or a group of the formula $>N — R_5$, wherein $R_5$ is a hydrogen atom or a $C_{1-4}$ alkyl group; and Z is a $C_{2-5}$ alkylene, which may optionally contain one oxygen atom among the chain carbon atoms, and may be optionally substituted by one or two $C_{1-4}$ alkyl or a group of the formula which comprises contacting in a solvent selected from the group consisting of ethanol and dimethyl sulfoxide in the presence or absence of potassium hydroxide at a temperature of from room temperature to the boiling point of the solvent used a trihaloacetamidophenyl ketone derivative of the formula,

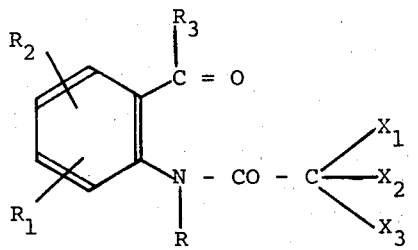

(II)

wherein $R_1$, $R_2$, $R_3$ and R are the same as defined above, and $X_1$, $X_2$ and $X_3$ are same or different halogen atoms, with an amine of the formula, $$HY - Z - NH_2$$ (III)

wherein Y and Z are as defined above.

2. A process according to claim 1, wherein the reaction is carried out in the presence of potassium hydroxide.

* * * * *